United States Patent
Collins

(10) Patent No.: US 12,097,471 B2
(45) Date of Patent: Sep. 24, 2024

(54) NANOPARTICLES FOR USE IN MEMBRANES

(71) Applicant: Evoqua Water Technologies LLC, Pittsburgh, PA (US)

(72) Inventor: Gregory R Collins, Monroe, NY (US)

(73) Assignee: Evoqua Water Technologies LLC, Pittsburgh, PA (US)

( * ) Notice: Subject to any disclaimer, the term of this patent is extended or adjusted under 35 U.S.C. 154(b) by 739 days.

(21) Appl. No.: 17/294,886

(22) PCT Filed: Nov. 15, 2019

(86) PCT No.: PCT/US2019/061659
§ 371 (c)(1),
(2) Date: May 18, 2021

(87) PCT Pub. No.: WO2020/106565
PCT Pub. Date: May 28, 2020

(65) Prior Publication Data
US 2021/0402355 A1    Dec. 30, 2021

Related U.S. Application Data

(60) Provisional application No. 62/770,233, filed on Nov. 21, 2018.

(51) Int. Cl.
*B01D 67/00* (2006.01)
*A61M 1/16* (2006.01)
(Continued)

(52) U.S. Cl.
CPC ........... *B01D 67/0079* (2013.01); *A61M 1/16* (2013.01); *B01D 61/027* (2013.01); *B01D 69/02* (2013.01);
(Continued)

(58) Field of Classification Search
CPC .. B01D 67/0079; B01D 61/027; B01D 69/02; B01D 69/10; B01D 69/144; A61M 1/16; C02F 1/442
See application file for complete search history.

(56) References Cited

U.S. PATENT DOCUMENTS

| | | |
|---|---|---|
| 5,779,897 A | 7/1998 | Kalthod et al. |
| 8,007,573 B2 | 8/2011 | Bansal et al. |

(Continued)

FOREIGN PATENT DOCUMENTS

| | | |
|---|---|---|
| CN | 101934219 | 1/2011 |
| CN | 103889562 | 6/2014 |

(Continued)

OTHER PUBLICATIONS

Graham et al. "Nanodetoxification: emerging role of nanomaterials in drug intoxication treatment" NIH Public Access. May 1, 2012 (May 1, 2012) p. 1-15; p. 3. para 2, p. 10. https://www.ncbi.nlm.nih.gov/pmc/articles/PMC3196307/.

(Continued)

*Primary Examiner* — Chester T Barry

(57) ABSTRACT

The present invention is directed to asymmetric membranes and methods for making such membranes, wherein the membranes have a void volume and nanoparticles located in the void volume. The membranes have a variety of applications, including blood purification, water purification, water decontamination and bioprocessing.

10 Claims, 2 Drawing Sheets

(51) Int. Cl.
  *B01D 61/02* (2006.01)
  *B01D 69/02* (2006.01)
  *B01D 69/10* (2006.01)
  *B01D 69/14* (2006.01)
  *C02F 1/44* (2023.01)

(52) U.S. Cl.
  CPC .......... *B01D 69/10* (2013.01); *B01D 69/144* (2013.01); *C02F 1/442* (2013.01); *B01D 67/0088* (2013.01); *B01D 2323/286* (2013.01); *B01D 2323/42* (2013.01); *B01D 2325/0233* (2022.08); *B01D 2325/20* (2013.01); *C02F 2303/04* (2013.01)

(56) References Cited

U.S. PATENT DOCUMENTS

| | | | |
|---|---|---|---|
| 8,029,857 | B2 | 10/2011 | Hoek et al. |
| 8,048,317 | B2 | 11/2011 | Rima et al. |
| 8,297,449 | B2 | 10/2012 | Afzali-Ardakani et al. |
| 8,906,673 | B2 | 12/2014 | Vu et al. |
| 9,033,908 | B2 | 5/2015 | Schilthuizen et al. |
| 9,233,518 | B2 | 1/2016 | Kang et al. |
| 9,403,678 | B2 | 8/2016 | Nikoobakht |
| 10,143,972 | B2 | 12/2018 | Li et al. |
| 2008/0237126 | A1* | 10/2008 | Hoek ................. B01D 69/1214 977/773 |
| 2012/0199528 | A1 | 8/2012 | Beplate |
| 2014/0319044 | A1 | 10/2014 | Giannelis et al. |
| 2016/0088756 | A1 | 3/2016 | Ramadas |
| 2016/0229969 | A1 | 8/2016 | Wiesner et al. |
| 2018/0085517 | A1 | 3/2018 | Laurence et al. |

FOREIGN PATENT DOCUMENTS

| | | |
|---|---|---|
| EP | 1509314 | 3/2005 |
| EP | 3144052 | 3/2017 |
| JP | 2011156519 | 8/2011 |
| WO | 2008/110172 | 9/2008 |
| WO | 2009/039467 | 3/2009 |
| WO | 2010002830 | 1/2010 |
| WO | 2014/095751 | 6/2014 |

OTHER PUBLICATIONS

International Preliminary Report on Patentability mailed Jun. 3, 2021, of PCT Application No. PCT/US19/61659 filed Nov. 15, 2019.

International Search Report and Written Opinion of the International Searching Authority Dated Apr. 14, 2020 of International PCT Application No. PCT/US2019/61659 filed Nov. 15, 2019.

Peer Contribution by China National Intellectual Property Feb. 3, 2020, of International PCT Application No. PCT/US2019/61659 filed Nov. 15, 2019.

Peer Contribution by European Patent Office Feb. 5, 2020, of International PCT Application No. PCT/US2019/61659 filed Nov. 15, 2019.

Peer Contribution by Japan Patent Office Jan. 29, 2020, of International PCT Application No. PCT/US2019/61659 filed Nov. 15, 2019.

Peer Contribution by Korean Intellectual Property Office Feb. 3, 2020, of International PCT Application No. PCT/US2019/61659 filed Nov. 15, 2019.

Amin, M.T., et al. "A review of removal of pollutants from water/wastewater using different types of nanomaterials". Advances in Materials Science and Engineering, vol. 2014, Article ID 825910.

Limo, M. J. et al. (2018). Interactions between Metal Oxides and Biomolecules: From Fundamental Understanding to Applications. Chemical Reviews, 118(22), 11118-11193. https://doi.org/10.1021/acs.chemrev.7b00660.

* cited by examiner

NANOPARTICLES FOR USE IN MEMBRANES

PRIORITY CLAIM

This application claims priority to and the benefit of U.S Provisional application with Ser. No. 62/770,233 filed on Nov. 21, 2018, entitled NANOPARTICLES FOR USE IN MEMBRANES, which is herein incorporated by reference in its entirety.

BACKGROUND

Nanotechnology (and use of nanoparticles) has found applications across a broad range of areas which include medicine, environmental uses, manufacturing, chemical-based sensors, energy, electronics, and consumer products. It has been described in the literature that nanoparticles can exhibit properties that result in, or improve product performance properties related to adsorption, absorption, anti-fouling, anti-oxidant, anti-bacterial, cell-targeted drug delivery, protein-targeted removal, virus inactivation, magnetic properties, and localized heating for sanitization purposes. Examples of membrane-based products that may take advantage of properties that nanoparticles can offer, such as used for purification and/or filtration of various fluids, are described below.

SUMMARY

In one aspect the invention is directed to asymmetric membranes having void volumes and nanoparticles located in the void volumes.

In one embodiment, the membrane is an asymmetric membrane for blood purification comprising nanoparticles located in a void volume of the membrane having a high affinity for blood toxins or biomolecules. In some embodiments the nanoparticles are gold, silver, silica or polymer nanoparticles that have a functionalized coating with active groups such as carboxyl, amine and NHS and/or are conjugated with secondary antibodies, biotin, avidin, streptavidin, protein A, protein G, or albumin (BSA). In other embodiments the nanoparticles have a high affinity for paraproteins, autoantibodies, toxins, drugs, circulating immune complexes, or soluble mediators of inflammatory response.

In another embodiment, the membrane is an asymmetric membrane for water purification comprising nanoparticles located in a void volume of the membrane for destroying or inactivating bacteria. In some embodiments the nanoparticles are silver or titanium oxide.

In another embodiment, the membrane is an asymmetric membrane for water purification comprising nanoparticles located in a void volume of the membrane that break down oil into biodegradable compounds. In some embodiments the nanoparticles are copper tungsten oxide or iron.

In another embodiment, the membrane is an asymmetric membrane to remove contaminants from water comprising nanoparticles located in a void volume of the membrane that are charged or are capable of hydrophilic/hydrophobic binding. In some embodiments the nanoparticles are charged silver, charged gold, charged polystyrene with trialkyammonium functional groups, monodisperse magnetite, iron-manganese, hydrous titanium dioxide, hydrous cerium oxide nanoparticles, or carbon nanotubes.

In another embodiment, the membrane is an asymmetric bioproces sing membrane comprising nanoparticles located in a void volume of the membrane that purify biopharmaceutical drugs derived from cell cultures and/or lysed cell suspensions. In some embodiments the nanoparticles are gold, silver, silica or polymer nanoparticles that have a conjugated ligand site, such as protein A, protein G, biotin, avidin, streptavidin, or albumin.

In another aspect, the present invention provides a method of making a membrane comprising nanoparticles. In one embodiment, the method includes the steps of providing an asymmetric membrane comprising a membrane skin layer with a predetermined pore size at a first outer surface of the membrane, an internal porous support structure of the membrane having a void volume, and a second outer porous surface of the membrane in fluid communication with the internal void volume of the membrane; filling said void volume with a nanoparticle solution through said porous surface of the membrane wherein the nanoparticles penetrate through the second outer surface into the void volume of said membrane without passing through the pores of said membrane skin layer; and drying the membrane with the nanoparticles in the void volume of the membrane.

In another embodiment the method includes preparing a membrane containing nanoparticles comprising the steps of providing an asymmetric membrane comprising a membrane skin layer with a predetermined pore size at a first outer surface of the membrane, an internal porous support structure of the membrane having a void volume, and a second outer porous surface of the membrane in fluid communication with the internal void volume of the membrane; filling said void volume with a nanoparticle solution through said porous surface of the membrane wherein the nanoparticles penetrate through the second outer surface into the void volume of said membrane without passing through the pores of said membrane skin layer; drying the membrane with the nanoparticles in the void volume of the membrane, and constructing a porous sealing layer at said second outer membrane surface, said sealing layer containing the nanoparticles within the void volume of the membrane.

While multiple embodiments are disclosed, still other embodiments of the present disclosure will become apparent to those skilled in the art from the following detailed description, which shows and describes illustrative embodiments of the invention. Accordingly, the detailed description is to be regarded as illustrative in nature and not restrictive.

DETAILED DESCRIPTION

Figure 1:
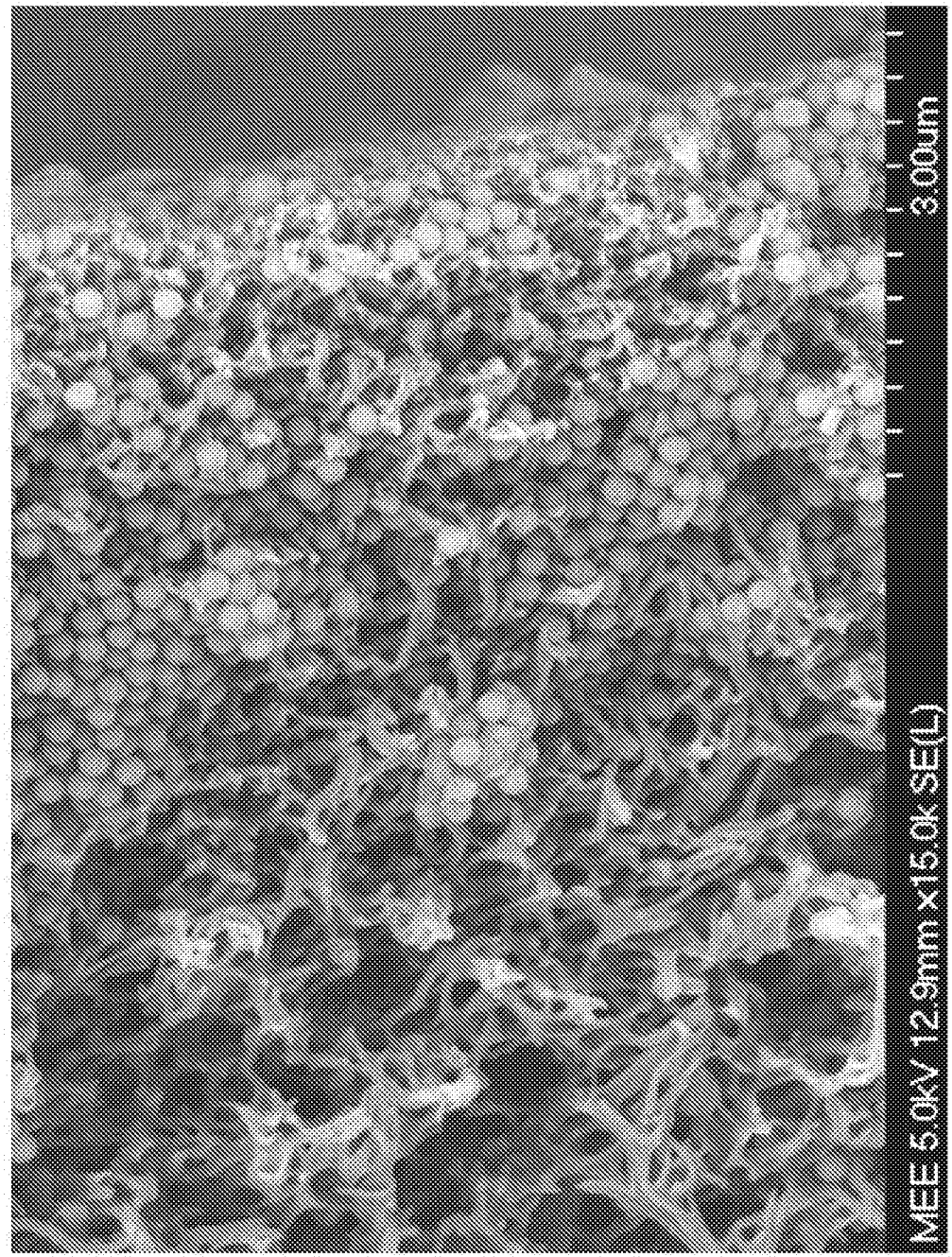
FIG. 1 is an SEM image of a cross-section of a FiberFlo 50 Hollow Fiber membrane containing 200 nm diameter nanoparticles.

Current methods for making nanoparticle-containing membranes mix nanoparticles into a dope solution before it is made into a membrane, making it necessary to modify the membrane spinning process to get a membrane with the desired characteristics and properties. Using this processing, nanoparticles become partially embedded in the base membrane polymer which limits their effectiveness and available surface area. One object of the invention is to incorporate the nanoparticles into the void volume (open space) of an existing asymmetric membrane rather than having the nanoparticles embedded in the base polymer layer; thus avoiding known complications. As described below, the methods of the present invention accomplish this with no changes to the membrane spinning process required and result in membranes where the entire surface area (or substantially the entire surface area) of the nanoparticle is functional. Depending upon the use and configuration of the devices of the present invention, the present invention includes a way to form a permeable sealing layer that effectively contains the nanoparticles within the void volume of the membrane.

In areas where membranes are used for blood purification, addition of nanoparticles that have a high affinity for blood toxins or biomolecules, such as proteins, can more effectively be used to treat patients with certain disease conditions that depend upon removal of specific substances from the patients (eg. paraproteins, autoantibodies, toxins, drugs, circulating immune complexes, or soluble mediators of inflammatory response). Examples of nanoparticles that could be used in this application include gold, silver, silica and polymer nanoparticles that have a functionalized coating with active groups such as carboxyl, amine and NHS and/or are conjugated with secondary antibodies, biotin, avidin, streptavidin, protein A, protein G, or albumin (BSA) such as provided by Creative Diagnostics (New York).

In areas where membranes are used for water purification, addition of silver or titanium oxide nanoparticles can be used to effectively destroy or inactivate bacteria that come in contact with the membrane. For example, titanium oxide nanoparticles can act as photocatalysts due to their ability to use light energy to start a chemical reaction that kills bacteria.

In areas where water may contain oil or organic solvent contamination, using photocatalytic copper tungsten oxide nanoparticles and iron nanoparticles are known to break down and decompose these into oil biodegradable compounds.

In addition, inclusion of charged nanoparticles or nanoparticles capable of hydrophilic/hydrophobic binding properties can be used to remove various contaminants from the purified water stream. For example, in settings where endotoxin is a common contaminate in medical grade water, using positively charged silver or gold nanoparticles or functionalized polystyrene nanoparticles using trialkylammonium ($NR_3^+$) groups to create a positively charged surface can bind endotoxin which carries a negative charge. In this case, a more open membrane may be used as a means to purify a higher volume of water while still being able to achieve the necessary endotoxin removal requirement. Arsenic is common ground water contaminate that is difficult to remove due to its low molecular weight and solubility in water. Using nanocrystals of monodisperse magnetite ($Fe_3O_4$), iron-manganese, hydrous titanium dioxide, hydrous cerium oxide nanoparticles, and carbon nanotubes have been demonstrated to have significant adsorption capacity in point-of-use water purification applications.

Bioprocessing is an application that purifies biopharmaceutical drugs derived from cell cultures and/or lysed cell suspensions that were used to produce the desired biological molecule. In these applications membranes are used for various separation processes and these generally are performed in series with affinity-based chromatography steps that serve to capture the biological molecules which are later eluted off from the chromatography resin as a critical purification step. The chromatography resins typically used are composed of porous beads (eg. agarose) that have a conjugated ligand attached to the surfaces of the porous beads that act as binding sites for the targeted biomolecule. The beads are generally packed into columns and require a minimum residence time to allow the diffusion of the biomolecule into the porous bead until it reaches a free binding site. Using a membrane containing nanoparticles such as gold, silver, silica or polymer nanoparticles that have a conjugated ligand site, such as protein A, protein G, biotin, avidin, streptavidin, or albumin (BSA) can then be effectively used to combine both a membrane separation step and a chromatography step into a single device which can reduce manufacturing cost in terms of labor and/or supplies used to produce the biopharmaceutical drug. It is also expected that one will achieve a better performance as the current porous bead technology becomes limited by diffusion of the target biomolecule into the depth of the porous bead. This is not the case using the membrane technology since convective transport of biomolecules into the membrane containing nanoparticles can easily be achieved by establishing a transmembrane pressure (TMP) and hence fluid flow across the membrane.

It should be understood to those skilled in the art that the invention is not limited to the above uses. In addition, the invention can include other functional particles, provided the asymmetric structure of the membrane is such that particles can enter into the more open pore structure and it can accommodate the functional particles within void volume of the membrane.

It is also understood that the disclosure should not be limited to only commercially available nanoparticles which are currently listed as follows:

1. Single Element Nanoparticles
Gold
Silver
Titanium
Aluminum
Bismuth
Boron
Carbon
Cobalt
Copper
Indium
Iron
Magnesium
Molybdenum
Nickel
Palladium
Rhodium
Ruthenium
Silicon
Sulfur
Tantalum
Tin
Tungsten
Zinc 2. Binary Compound Nanoparticles
Aluminum Hydroxide, Aluminum Nitride, Aluminum Oxide
Barium Oxide
Bismuth Oxide
Boron Carbide, Boron Nitride, Boron Oxide
Calcium Carbonate
Cerium Oxide
Chromium Oxide
Cobalt Oxide
Copper Oxide
Dysprosium Oxide
Erbium Oxide
Europium Oxide
Gadolinium Oxide
Hafnium Carbide, Hafnium Oxide Hydroxy Apatite
Indium Hydroxide, Indium Oxide
Iron Oxide
Lanthanum Oxide
Magnesium Oxide
Molybdenum Disulfide, Molybdenum Oxide
Neodymium Oxide
Nickel Oxide
Praseodymium Oxide
Samarium Oxide
Silicon Carbide, Silicon Oxide, Silicon Dioxide, Silicon Nitride
Tin Oxide
Titanium Carbide, Titanium Oxide, Titanium Dioxide, Titanium Nitride
Tungsten Carbide, Tungsten Disulfide, Tungsten Oxide
Yttrium Oxide
Zinc Carbide, Zinc Oxide
Zirconium Carbide, Zirconium Oxide
3. Complex/Coated Nanoparticles
Poly(lactic-co-glycolic acid) (PLGA)
Poly(methyl methacrylate) (PMMA)
Poly(ε-caprolactone) (PCL)
Polyacrylate (PA)
Polylactide (PLA)
Polystyrene (PS)
Zeolite Imidazolate
Aluminum Titanate
Antimony Tin Oxide
Barium Iron Oxide
Barium Sulfate
Barium Titanate
Barium Zirconium Titanate
Calcia Stabilized Zirconia
Calcium Carbonate
Calcium Zirconate
Carbide-derived Carbon
Cerium Gadolinium Oxide
Cesium Dihydrogenphosphate
Cobalt Carbon-Coated
Cobalt Ferrite
Cobalt Iron Oxide
Cobalt Zinc Ferrite
Copper Carbon-Coated
Copper Nickel Alloy
Copper Tin Alloy
Gallium Antimonide
Indium Oxide/Tin Oxide
Indium Tin Oxide
Indium Zinc Oxide
Iron Carbon-Coated
Iron Cobalt
Iron Nickel
Lanthanum Calcium Manganese Oxide
Lanthanum Chromium Oxide
Lanthanum Hexaboride
Lanthanum Strontium Manganate Oxide
Lithium Titanium Oxide
Magnesium Aluminate
Nickel Carbon-Coated
Nickel Iron Oxide
Nickel Zinc Ferrite
Samarium Cerium Oxide
Silicon Nitride/carbide
Silver Palladium
Strontium Carbonate
Strontium Hexaferrite
Strontium Hexaluminate
Strontium Titanate
Strontium Titanium oxide
Titanium Boride
Titanium Boride/Boron Carbide
Titanium Boride/Boron Carbide/Tungsten Boride
Titanium Carbide/Nitrogen
Titanium Carbonitride
Tungsten Carbide/Cobalt
Ytterbium Fluoride
Yttria Stabilized Zirconia
Yttrium Iron Garnet
Yttrium-Aluminum Oxide
Zinc Ferrite
Zinc Oxide (Al-doped)
Zinc Oxide (Ga-doped)
Zirconia
Zirconium Diboride
Gold, Silver, Silica, Titanium, and Polymers coated with:
    Albumin
    Amine
    Anidin
    Biotin
    Butyl
    C18
    Carboxyl
    EDTA
    Epoxy
    Hydroxyl
    IgG Antibody
    Galactose
    Glutathione
    NHS
    NTA
    NR3+
    Ni-NTA
    Phenyl
    Protein-A
    Protein-G
    PVP
    PEG
    Streptavidin
    Sulfate

EXAMPLES OF NANOPARTICLE FILLED MEMBRANES

Example I

An asymmetric polysulfone membrane containing positively charged nanoparticles is prepared by taking a finished hollow fiber capsule filter device configured with a U-shaped fiber bundle and potted at one end to form a tube sheet and passing an aqueous solution containing positively charged nanoparticles through the membrane.

Positively charged nanoparticles can be obtained commercially, such as polystyrene nanoparticles that are functionalized by attaching trialkylammonium ($NR_3^+$) groups on the surface of the polystyrene (DiagPoly™ $NR_3^+$ Polystyrene Nanoparticles, 100 nm diameter, Creative Diagnostics), or alternatively can be synthesized, such as positively charged, stabilized silver nanoparticles. The synthesis of positively charged, stabilized silver nanoparticles (AgNPs, 110 nm diameter with a positive charge of +55 mV) is performed by taking 1 g polyethylenimine (PEI; molecular weight 25 000 g mol$^{-1}$) and dissolving it in 40 g water and then heating to 90° C. Then, 0.5 g $AgNO_3$ dissolved in 1 mL water is quickly added with the dispersion kept at 90° C. for 1 hr and allowed to cool down to room temperature. Charged silver nanoparticles are collected by ultracentrifugation (3 times, 30 000 rpm, 30 min) and subsequently re-dispersed in pure water and stored at 4° C. until use.

Figure 2:
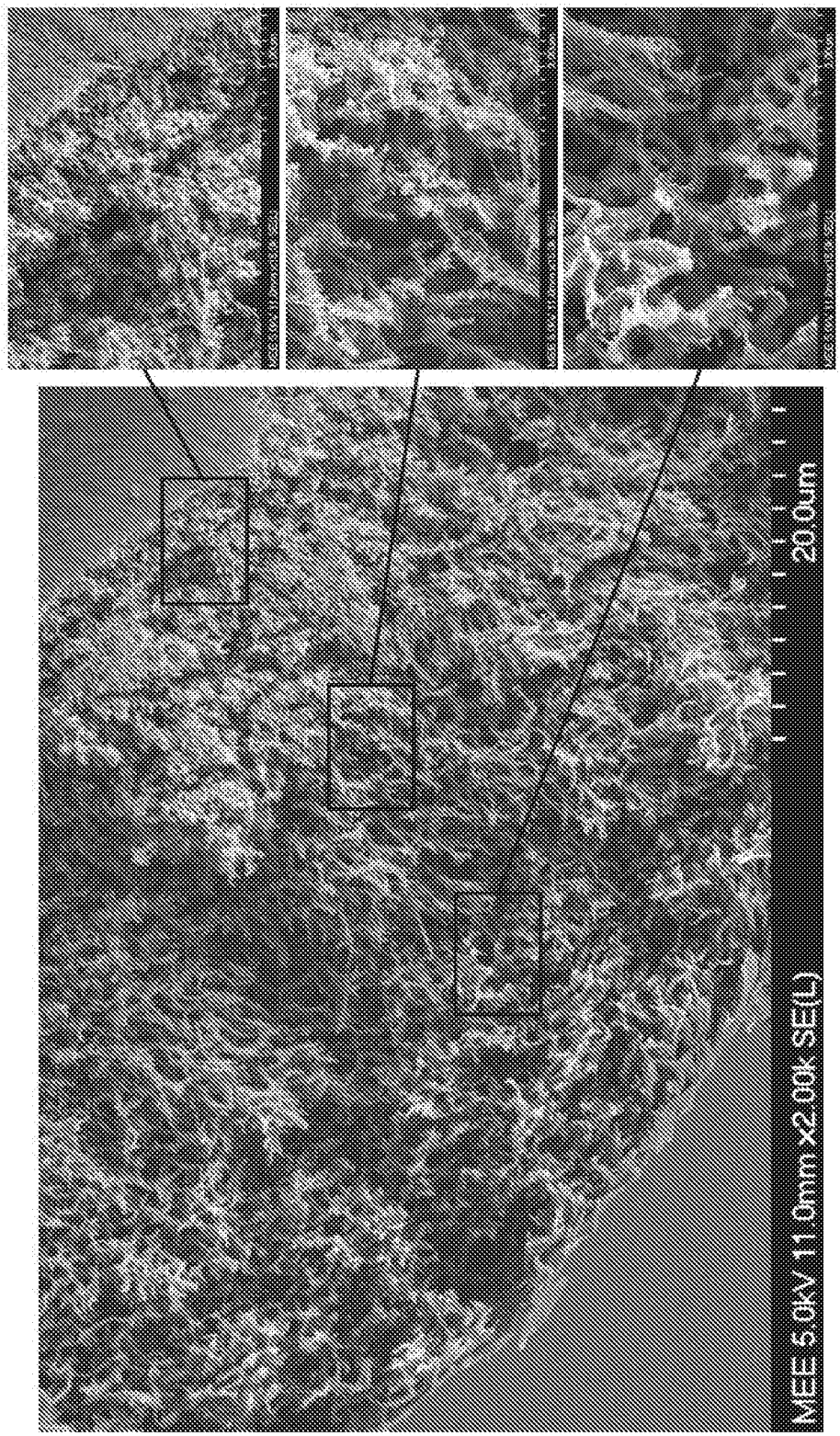
FIG. 2 is an SEM image of a cross-section of a FiberFlo 50 Hollow Fiber membrane containing 100 nm nanoparticles.

For internally skinned hollow fiber membranes where the tight membrane is at the inside wall of the hollow fiber, the direction of flow of the nanoparticle solution through the membrane is from outside the hollow fiber to the inside lumen of the hollow fiber which needs to be the flow direction during operation of the device. This is accomplished using a pump while monitoring the pump outlet pressure so as not to exceed the collapse pressure of the hollow fiber membrane. With a membrane pore size of 0.05 microns (50 nm), such as the FiberFlo 50 Hollow Fiber membrane (Mar Cor Purification), 200 nm or 100 nm nanoparticles enter the membrane from the outside wall and will not pass through the tight skin layer of the membrane which has a pore size of 50 nm. By controlling the concentration of the nanoparticle solution, the rate at which the solution is being pumped through the membrane, and the total volume of solution used, nanoparticles can fill into the void space of the membrane to a desired level. As shown in FIG. 1, which is an SEM cross section of a FiberFlo 50 Hollow Fiber membrane containing 200 nm diameter nanoparticles, the nanoparticles are shown packed into the void volume at the inner skin layer of the membrane. As shown in FIG. 2, which is an SEM cross section of a similar FiberFlo 50 Hollow Fiber membrane but contains smaller 100 nm nanoparticles, the nanoparticles are more densely packed into the void volume at the inner skin layer of the membrane (upper close-up sectional view), relative to the two mid-membrane points of the membrane (middle and lower close-up sectional views). It should be understood to those skilled in the art that optimal conditions of flow rate and nanoparticle concentration will be specific to the size, shape and surface properties of the nanoparticles being selected and the asymmetric membrane being used. This to ensure proper filling of the membrane void volume without creating a damming effect whereby nanoparticles can build-up at the entry point instead of filling the void volume.

After passing the solution through the membrane, the filter can be placed in an oven at 50-60° C. until dry.

To verify performance of this membrane, the filter is challenged with an endotoxin solution such that a log reduction of endotoxin is measured and compared to a control filter device that does not contain positively charged silver nanoparticles.

Example II

In a manner similar to Example I, positively charged silver nanoparticles are prepared and stored as an aqueous solution. In this example, however, the filter compartment in contact with the outside surface of the hollow fiber is filled with the nanoparticle solution, and the filter membrane is effectively dry and is composed of a hydrophilic material that draws the nanoparticle solution into the internal space of the membrane wall by capillary action which does not require a pump. After the compartment is filled, the filter unit is placed into an oven at 50-60° C. and dried. It is understood that as the water evaporates from the filter, the concentration of nanoparticles increases while continuing to be drawn into the membrane wall by capillary action.

Additional examples using this approach may likewise be obtained by repeating the above multiple times to achieve higher concentrations of nanoparticles inside the void volume of the membrane wall.

Example III

A device targeted to remove a specific antibody from blood, such as Antimyelin Ab for treatment of Multiple Sclerosis, is made using an asymmetric polysulfone membrane containing gold nanoparticles that are coated with the amino acid tryptophan. Functionalization of the gold nanoparticles (50-200 nm) is carried out by slowly adding either 0.2 ml or 0.4 ml of 10 mM tryptophan aqueous solution (Trp) into 10 ml of a gold nanoparticle colloid solution under constant stirring for 30 min to obtain molar ratios of gold: tryptophan in the resulting gold-tryptophan colloids at 1:1 and 1:2, respectively. Tryptophan-functionalized gold nanoparticles are separated by the centrifugation at 19,900 rpm for 90 min and subsequently re-dispersed in water for storage.

In a manner consistent with Example II, the compartment of a dry filter in direct contact with the more open side of the asymmetric membrane is filled with the colloidal solution of tryptophan coated gold nanoparticles whereby the solution is drawn into the membrane wall by capillary action. To further promote more nanoparticles entering the void volume of the membrane, air pressure (10-30 psi) is applied to this compartment to drive any fluid external to the outside surface of the membrane into the wall of the membrane while allowing excess fluid to pass through and into the lumen side of the membrane. Once complete, the filter is dried in an oven at 50-60° C.

To seal the nanoparticles inside the void volume of the membrane, a thin film composite ultrafiltration membrane is formed on the outside wall of the membrane by first dissolving a sodium salt of polystyrene sulfonate and polyvinyl benzyl trimethylammonium chloride in equal amounts of ethyl alcohol and concentrated hydrochloric acid to provide a stock solution containing about 20% by weight of the solid polyelectrolyte complex after removal of the precipitated salt by centrifugation. Following this, the stock solution is diluted with a solution containing equal amount of ethyl alcohol and concentrated hydrochloric acid to create a solution containing 0.2% by weight of the polyelectrolyte complex. To form the desired sealing membrane on the outside of the hollow fiber, a quantity sufficient of the polyelectrolyte complex solution to coat the outside surface of the membrane is introduced into the filter compartment in contact with the outside wall of the membrane. The filter is then quickly inverted several times to evenly cover all the hollow fibers. Any excess solution is shaken out through the filter side ports and the filter is placed in an oven at 60° C. for a period necessary to cure the membrane.

Example IV

For a bioprocessing application, a filter membrane device containing a functionalized nanoparticle with a conjugated Protein-A ligand is prepared as follows. In a manner consistent with Example III, an aqueous colloidal solution containing Protein A conjugated polystyrene nanoparticles (200 nm) is introduced into an asymmetric membrane as part of a filter device and allowed to dry.

To form the sealing layer, first an aqueous phase is prepared by dissolving piperazine (PIP) (0.25 wt %), sodium carbonate ($Na_2CO_3$) (0.1 wt %, as acid acceptor), sodium dodecyl sulfate (SDS) (0.1 wt %, as surfactant) in deionized water. A quantity sufficient of the piperazine solution to fill the void volume of the membrane is introduced into the filter compartment in contact with the outside wall of the membrane and kept for 10 min while inverting several times to evenly wet all the hollow fibers in the device. After draining off excess solution through the filter side ports, the membrane is dried in air to vaporize the unbound water. Afterwards, a hexane solution containing 0.1 wt % trimesoyl chloride (TMC) is introduced to membrane surface (saturated with the PIP) to initiate the polymerization reaction between PIP and TMC at the water-hexane interface. After 2 min, the excess hexane solution is poured out of the filter through the side ports and membrane dried in air for 120 min to evaporate the n-hexane. Finally, the filter device is placed into an oven at 70° C. for 60 min, and then washed and stored in water for at least 24 hr.

Example V

For a bioprocessing application, a filter membrane device containing a functionalized nanoparticle with a conjugated Protein-A ligand is prepared as follows. In a continuous phase inversion process used to make an asymmetric membrane whereby the membrane has been generally formed after the dope solution has been exposed to the precipitating solution and there has been a sufficient exchange of solvent and non-solvent to precipitate the polymer and form the porous membrane, nanoparticles are introduced in the process without altering the original asymmetric membrane formulation. The membrane is rinsed to remove residual solvent and dried, then submerged in an aqueous solution containing Protein A conjugated polystyrene nanoparticles (200 nm) for a time sufficient to fill the void volume of the membrane with the colloidal solution. The membrane is then passed through an air knife to remove excess fluid from the surface of the membrane and the membrane is again dried.

To form the sealing layer, dried membrane containing nanoparticles is submerged in an aqueous solution containing piperazine (PIP) (0.25 wt %), sodium carbonate ($Na_2CO_3$) (0.1 wt %, as acid acceptor), and sodium dodecyl sulfate (SDS) (0.1 wt %, as surfactant) as described in Example IV for a time sufficient to fill the void volume of the membrane. The membrane is then passed through an air knife to remove excess solution from the surface and vaporize the unbound water. The membrane containing the nanoparticles and aqueous PIP solution is then submerged into a hexane solution containing 0.1 wt % trimesoyl chloride (TMC) to initiate the polymerization reaction between PIP and TMC at the water-hexane interface for a period of time sufficient to form the thin sealing layer. Upon exiting the hexane solution, excess hexane solution is removed using an air knife and the membrane is dried sufficiently to evaporate the hexane. The membrane is further washed by rinsing with water and finally dried by passing through an oven or by contacting a heated drum at 70° C. for a period of time to dry the membrane. The membrane may be wound or collected to form bundles to be used to make filter devices.

Example VI

Using the method described in Example V to introduce nanoparticles into the void volume of an asymmetric membrane spinning process, a method to seal the open spongey side of the membrane is performed by laser induction using $CO_2$ pulsed lasers (10-150 W) focused at the external surfaces of the membrane under atmospheric conditions. Laser duty cycles of 1-5% is used to form a porous layer (5-10 microns thick) whereby high localized temperatures (>2500° C.) break the polymer bonds of the base membrane and rearrange to form a structure capable of containing the nanoparticles during subsequent use.

Various embodiments of this disclosure have been described above for purposes of illustrating the details thereof and to enable one of ordinary skill in the art to make and use the disclosed technology. The details and features of the disclosed embodiments are not intended to be limiting, as many variations and modifications will be readily apparent to those of skill in the art. Accordingly, the scope of the present disclosure is intended to be interpreted broadly and to include all variations and modifications coming within the scope and spirit of the appended claims and their legal equivalents.

What is claimed is:

1. A method of preparing a membrane containing nanoparticles comprising the steps of:
providing an asymmetric membrane comprising a membrane skin layer with a predetermined pore size at a first outer surface of the membrane, an internal porous support structure of the membrane having an internal void volume, and a second outer porous surface of the membrane in fluid communication with the internal void volume of the membrane;
filling said void volume with a nanoparticle solution through said second porous surface of the membrane wherein the nanoparticles penetrate through the second outer surface into the void volume of said membrane without passing through the pores of said membrane skin layer.

2. The method of claim 1 further comprising the step of drying the asymmetric membrane with the nanoparticles in the void volume of the membrane.

3. The method of claim 1 wherein the asymmetric membrane comprises an element of a filtration device.

4. The method of claim 1 wherein the asymmetric membrane comprises a flat sheet or hollow fiber membrane.

5. The method of claim 1 wherein nanoparticles are transported into the void volume of the membrane by i) wetting the membrane wherein nanoparticle solution is drawn into the membrane by capillary action; ii) pushing the nanoparticle solution into the membrane by applying a pressure gradient across the membrane; or iii) diffusion whereby the membrane is wetted and placed in contact with the nanoparticle solution.

6. The method of claim 1, wherein nanoparticles have at least one of the following characteristics:
a) charged surfaces for binding of oppositely charged molecules;
b) hydrophobic and/or hydrophilic surfaces for binding of nonpolar/polar molecules;
c) conjugated ligands and/or surface coatings for binding of target biological molecules and/or cells; or
d) photocatalytic properties used for destruction of bacteria.

7. The method of claim 1, further comprising the step of forming a permeable sealing layer on the membrane.

8. A method of preparing a membrane containing nanoparticles comprising the steps of:
providing an asymmetric membrane comprising membrane skin layer with a predetermined pore size at a first outer surface of the membrane, an internal porous support structure of the membrane having a void volume, and a second outer porous surface of the membrane in fluid communication with the void volume of the membrane;

filling said void volume with a nanoparticle solution through said second outer porous surface of the membrane wherein the nanoparticles penetrate through the second outer surface into the void volume of said membrane without passing through the pores of said membrane skin layer; and constructing a porous sealing layer at said second outer membrane surface, said sealing layer containing the nanoparticles within the void volume of the membrane.

9. The method of claim 8 wherein the porous sealing layer comprises i) a polyelectrolyte complex coating at said second outer surface to form a composite thin film membrane at outer membrane surface; ii) a composite thin film membrane formed at the outer membrane surface; or iii) a rearranged second outer surface formed with a laser to generate high localized temperatures at the second outer surface to break and rearrange the base membrane polymer bonds to form a rearranged porous structure.

10. The method of claim 8 further comprising the step of drying the asymmetric membrane and porous sealing layer with the nanoparticles in the void volume of the membrane.

* * * * *